United States Patent [19]
Golukhov et al.

[11] Patent Number: 5,316,732
[45] Date of Patent: May 31, 1994

[54] EXTRACTION VIAL

[75] Inventors: Albert Golukhov, Mountain View; Josefina T. Baker, Cupertino; Richard S. Matusewicz, San Jose, all of Calif.

[73] Assignee: Smithkline diagnostics, Inc., San Jose, Calif.

[21] Appl. No.: 907,359

[22] Filed: Jul. 1, 1992

[51] Int. Cl.$^5$ ............................................. B01L 3/00
[52] U.S. Cl. ..................................... 422/102; 422/99; 422/101; 435/296; 206/438; 206/570
[58] Field of Search ............... 422/99, 101, 102; 435/296, 299; 436/177, 178; 128/760, 767, 749; 206/438, 570

[56] References Cited

U.S. PATENT DOCUMENTS

| | | | |
|---|---|---|---|
| 3,777,949 | 12/1973 | Chiquiari-Arias | 222/541 |
| 3,819,045 | 6/1974 | Greenwald | 436/178 |
| 3,865,551 | 2/1975 | Saiki et al. | 422/99 |
| 4,022,576 | 5/1977 | Parker | 436/177 |
| 4,314,993 | 2/1982 | Wijnendaele | 530/389.5 X |
| 4,566,613 | 1/1986 | Anscomb | 222/541 |
| 4,678,559 | 7/1987 | Szabados | 422/101 X |
| 4,787,536 | 11/1988 | Widerström | 222/541 X |
| 4,849,173 | 7/1989 | Chang | 422/56 |
| 4,859,610 | 8/1989 | Maggio | 422/102 X |
| 5,040,706 | 8/1991 | Davis et al. | 604/295 X |
| 5,064,766 | 11/1991 | Wardlow | 436/66 |
| 5,066,463 | 11/1991 | Chang | 422/58 X |
| 5,198,365 | 3/1993 | Grow et al. | 436/177 X |

*Primary Examiner*—James C. Housel
*Assistant Examiner*—Maureen M. Wallenhorst
*Attorney, Agent, or Firm*—William H. May; Gary T. Hampson

[57] ABSTRACT

An extraction vial includes a reservoir portion having generally parallel walls, a neck portion defining an opening into the reservoir portion and a channel surrounding the opening, a nozzle portion integral with reservoir portion at a second end of the reservoir, a sealing closure that closes the nozzle, a base integral with the sealing closure and including a support surface adapted to support the vial in an upright position, and a cap received and removably maintained within the channel. An extraction liquid may be contained within the vial for extracting sample from a carrier. The vial may be used by adding the carrier to the extraction liquid within the vial, closing the vial with the cap, agitating the vial to release sample from the carrier, and removing at least the sealing closure or, preferably, the sealing closure and base whereby extraction liquid can be expelled from the vial.

4 Claims, 1 Drawing Sheet

EXTRACTION VIAL

FIELD OF THE INVENTION

The present invention is directed to immunochemical testing in general, and in particular to extraction vials and kits comprising an extraction solution for use in extracting an analyte from a test sample for deposit of the analyte onto a testing device.

BACKGROUND OF THE INVENTION

Diagnostic test matrices have revolutionized the health care industry by focusing on relatively easy-to-use devices. For examples, pregnancy-testing dip sticks are commonplace in market facilities throughout the world. Fecal occult monitoring devices, such as the Hemoccult ® brand fecal occult blood test, allow for obtaining samples in the privacy of the patient's home whereby analysis of the sample can be accomplished at a screening facility.

Another form of such test matrices are chromatographic-type assaying systems. Chromatographic-type assaying systems have enjoyed widespread use in the diagnostic fields for several years. Such devices typically rely upon a format whereby a solution comprising a carrier solvent and a test sample suspected of containing an analyte to be detected, is applied to a thin, flat, absorbent medium, which typically has incorporated thereon a binding partner to the analyte. The solution is applied to the absorbent medium and moves along the medium by way of capillary action. A labeling scheme is then utilized to determine the presence of the immobilized analyte. This type of assay is generally referred to as an "immunochromatographic assay". There are two types of immunochromatographic assay types, generally referred to as "sandwich", or "capture", immunochromatographic assays, and "competitive" immunochromatographic assays.

Sandwich immunochromatographic assays typically involve mixing a sample containing an analyte of interest with either a monoclonal or polyclonal "capture" antibody to the analyte (alternatively, the sample can be added directly to a chromatographic medium having affixed thereto the capture antibody). The antibody can be conjugated to some form of label, for example, colored latex beads, chemiluminescent, enzymatic, fluorescent, radioactive, colloidal gold, etc. Thereafter, an analyte-labeled antibody complex is formed. This complex is then applied to the chromatographic medium which has a second monoclonal antibody or additional polyclonal antibodies immobilized thereon. As the complex moves along the medium, the analyte-labeled antibody complex becomes bound to the immobilized antibody, forming an immobilized antibody-analyte-labeled antibody complex. The label can then be read to provide an indication of the presence (and quantity) of the analyte in the sample medium.

Competitive immunochromatographic assays typically involve mixing a sample containing an analyte of interest with a known quantity of the same analyte having a label conjugated thereto. This mixture is then added to a known quantity of immobilized antibody to the analyte. As the mixture moves along the medium, a competition is created between the sample-analyte and the labeled-analyte: the more sample-analyte available for binding to the immobilized antibody, the less label that will be detected. Thus, the amount of sample-analyte is inversely proportional to the amount of label obtained.

Immunochromatographic assays are not without drawbacks. For example, with respect to, e.g., fecal samples, mucous-based samples, throat or vaginal swabs, etc., it is very difficult to apply these materials to the chromatographic medium directly. Thus, these materials are usually applied to the chromatographic medium, whereupon a solvent solution is added thereto, the solvent being capable of carrying the analyte of interest to a particular location on the chromatographic medium. Problems arise using this approach because the materials can clog the pores of the chromatographic medium, making chromatographic analysis extremely difficult because of interference with the flow of the solvent caused by such clogging. Additionally, these materials can include therein extraneous matter which can interfere with the analysis due to, e.g., non-specific binding with the analyte antibodies, or interference with the particular label utilized for the analyses.

An alternative to this approach is to utilize extraction or pretreatment reactions whereby the sample material is added to a liquid extracting medium such that the sample is brought from its solid or semi-solid form to a liquid form. Conventionally, this is accomplished by a technician in a laboratory setting and is carried out in small transfer vessels, whereby the extraction medium containing the sample is added to the chromatographic medium via, e.g., a pipette. This scenario raises additional problems, particularly in the areas of contamination and waste disposal. Such problems are particularly relevant with respect to the possibility of transfer of communicable diseases to the technician(s), as well as the potential for cross-contamination of samples.

What is needed, in view of the foregoing, is a device that will readily facilitate the extraction of an analyte from a sample for analysis of material in the sample, and that ensures that contamination and waste byproducts are substantially minimized.

SUMMARY OF THE INVENTION

The present invention satisfies these needs. In accordance with the invention disclosed herein, a disposable extraction vial capable of containing or alternatively, containing liquid is provided. The extraction vial is adapted for receiving a diagnostic sample carrier such that removal of the sample from the carrier is facilitated by the interaction of the sample with the extraction liquid. The extraction vial is further adapted for controlled release of a desired amount of the extraction liquid comprising the diagnostic sample onto a diagnostic test platform. Beneficially, the extraction vial containing the sample carrier and extraction liquid remaining therein can be conveniently disposed as a single unit. Test kits comprising an extraction vial and a separately contained extraction medium for addition to the vial, are further disclosed.

BRIEF DESCRIPTION OF THE DRAWINGS

The following drawings are presented for the purpose of reference in conjunction with the Detailed Description of Preferred Embodiments of the Invention.

DETAILED DESCRIPTION OF PREFERRED EMBODIMENTS

Figure 1:
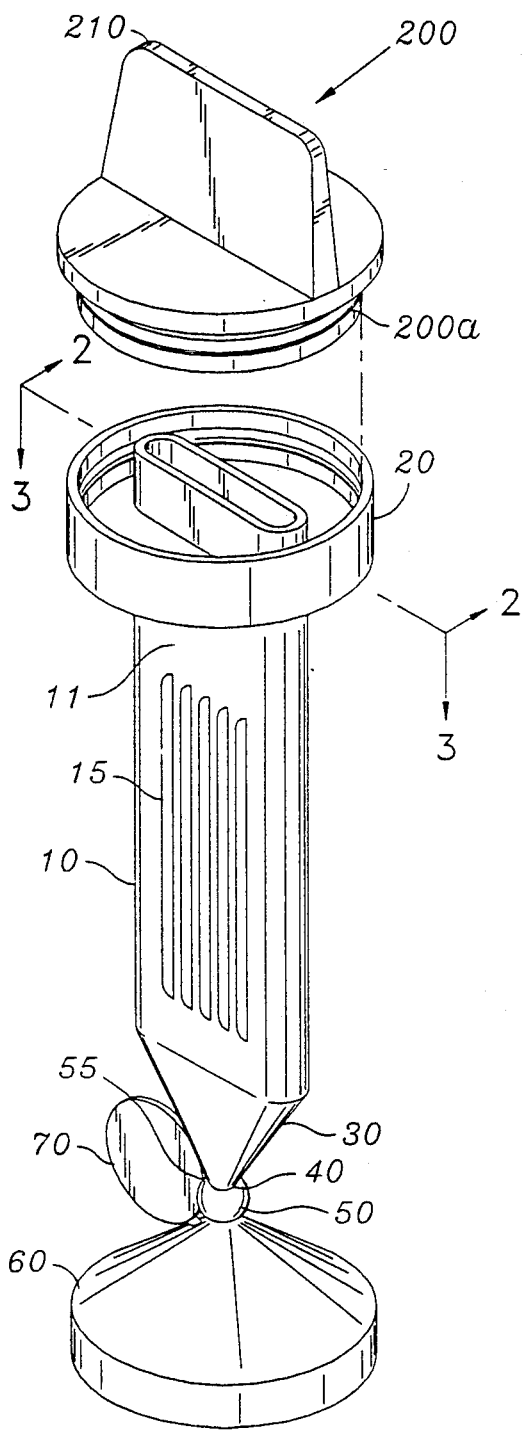
FIG. 1 is a perspective view of an embodiment of the disclosed extraction vial.

With the exception of certain clinical samples, for example, whole blood, serum, plasma, urine, cerebro spinal fluid, other clinical samples typically require a collection step and a liquid modification step before the sample can be analyzed via diagnostic assay procedures. (The aforementioned clinical samples can, however, be utilized in conjunction with the invention disclosed herein.) As used herein "other clinical samples" include solid-form or semi-solid form materials, for example, fecal materials, epidermal scrapes, mucous, throat, vaginal swabs, etc. As used herein "liquid modification step" is intended to mean steps taken to allow for a chromatographic-type flow of such other clinical samples along a diagnostic test platform; typically, this is manifested by totally or partially liquefying the solid-form or semi-solid form test sample so that analytes of interest interspersed therein can be examined via the diagnostic test protocols.

For ease of discussion and without the intention of limiting the types of clinical samples which can be utilized in conjunction with the disclosed extraction vial, the following discussion will focus on fecal materials as an example of an applicable clinical sample, and immunochromatographic assaying procedures. It is to be understood, however, that the disclosed extraction vial can be utilized with a myriad of diagnostic assaying procedures. I.e., the disclosed vial can be utilized in conjunction with diagnostic matrices such as the Hemoccult ® brand fecal occult blood test (SmithKline Diagnostics, Inc., San Jose, Calif., U.S.A.) whereby a fecal sample is extracted from a sample carrier into the extraction vial, and the extraction liquid, comprising the sample, is applied to, e.g., a guaiac-based assay device; developing solution can thereafter be applied to the device. Those in the art are credited with recognizing the advantages to be derived from utilizing the disclosed extraction vial in related diagnostic assaying protocols.

As is well known in the art, the presence of hemoglobin in fecal samples may be indicative of colon cancer; accordingly, screening of fecal samples for the presence of hemoglobin is routinely practiced. However, as is also well known, with respect to guaiac-based fecal occult screening devices, certain foods, e.g., red meats, vegetables, etc., can give false positive results. This is because blood present in meat, or peroxidases present in vegetables, may be present in the fecal sample, and these materials may indicate, erroneously, the presence of patient-derived hemoglobin in the fecal sample.

The advent of immunochemical testing protocols has helped to improve such screening. For example, antibodies specific for, e.g., human hemoglobin, can be utilized for the detection of human hemoglobin in fecal samples. Beneficially, diagnostic test devices can fully exploit the binding specificity of such antibodies. However, because of the chromatographic aspects of such devices, it is necessary for a liquid to be added to the device, typically at a region where antibodies specific to a desired analyte are located. For example, in a "dipstick" type diagnostic device, a portion of the device is "dipped" into a liquid sample or a liquid comprising a sample. A common form of this device is a pregnancy dipstick whereby antibodies specific for human chorionic gonadotropin ("HCG", indicative of pregnancy) are coated onto a portion of the dipstick; the dipstick is inserted into patient urine. Instantly, the chromatographic aspect of such a device draws the liquid sample up through the device, whereby interactions between patient HCG, HCG-specific antibodies and some form of labeled agent (typically a labeled antibody specific for an epitope on HCG other than the first antibody epitope) indicate the presence or absence of HCG.

With solid and semi-solid samples such as fecal samples, it is necessary to extract the analyte of interest. I.e., either a liquid can be added to such a sample which has been placed directly onto a diagnostic test device (as is the case with, e.g., Hemoccult ® brand fecal occult blood monitoring devices), or the sample can be added to a liquid which, in turn, is added to the test device. From a practical perspective, the latter protocol is utilized in that in order to liquify sample added directly to a device, sufficient liquid must be added thereto; this can often lead to (relative) excessive amounts of such a liquid such that the sample can be washed from the testing device, or contamination of the instrument used to add the liquid to the sample (e.g., a pipette tip coming into contact with the sample) can occur. Focusing on a typical method of practicing the former protocol, the incidence of cross-contaminations and waste disposal is increased. This is because sample carriers (i.e., some form of material to which the sample is applied) are added to, e.g., microtiter wells, and a liquid is added to the wells. Thereafter, liquid comprising the sample is removed from the wells and added to the diagnostic test device. Thus, it is possible (due to liquid splashing, etc.) to cross contaminate the wells. Additionally, the wells must be either disposed or thoroughly washed and cleaned after use.

These problems are avoided by use of the disclosed invention which provides a container comprising a body portion defining a chamber containing an extraction fluid, the body portion defining an opening for external access into the chamber and having a predefined line of weakness in the wall portion, whereby the line of weakness in the wall portion is broken to allow for the release of the solution, preferably without the need to utilize a cutting tool. In a particularly preferred embodiment of the invention, a disposable extraction vial is disclosed, the vial comprising an elongated hollow body comprising a reservoir portion constituted by a chamber bounded by a pair of spaced, flat, generally parallel, compressible walls, said chamber comprising an extraction liquid for expulsion upon compression of the walls; a neck portion integral with an area near an end of the reservoir portion, the neck portion comprising a channel for receiving a removable cap, the channel defined by the terminal end of the reservoir portion and the neck portion; a generally cylindrical nozzle portion integral with the end of the reservoir portion opposite the neck portion, the nozzle portion comprising a passage connecting with the chamber and a leading end, the leading end of the nozzle portion being angularly offset with respect to the longitudinal extent of the chamber; a sealing closure integral with and terminating the leading end of the nozzle portion and separated therefrom by a line of weakness, the connection between the sealing closure and the leading end being such that when sealing closure is broken, the free end of the nozzle portion presents a discharge opening; a support tab integral with, extending between and connecting said nozzle portion to the sealing closure to protect the nozzle portion against inadvertent disruption; and an extraction liquid adapted for use in diagnostic analysis of biological materials, the liquid located within reservoir portion.

Beneficially, the disclosed extraction vial avoids the problems noted above without compromising the testing procedure. By utilizing an extraction vial comprising an extraction liquid, a sample carrier (or a section thereof) is added directly to the vial whereby the sample material can be extracted from the carrier into the liquid. At an appropriate time, the liquid comprising the sample can be added to the diagnostic test device; thereafter, the vial containing the liquid and the sample carrier can be efficiently disposed. Advantageously, because the extraction liquid is located within the vial and the sample carrier is added thereto, problems and concerns associated with, e.g., cross-contamination, are avoided.

With reference to the figures and a particularly preferred embodiment of the extraction vial, the disposable extraction vial 100 comprises an elongated hollow body comprising a reservoir portion 10; a neck portion 20 integral with the reservoir portion; a nozzle portion 30 integral with the reservoir portion located opposite to the neck portion; a sealing closure 40 integral with and terminating the leading end 35 of the nozzle; a support tab or mechanism 70 integral with, extending between and connecting the nozzle portion to the sealing closure; and an extraction liquid 80 include within the reservoir portion.

Extraction vial 100 is preferably composed of a chemically inert material conducive to use in conjunction with biological and chemical samples. Exemplary materials include, but are not limited to, thermoplastics such as polypropylene, polyethylene, polynitrile, polyvinyl acetate, polyethylene terephthalate, polyethylene-vinyl acetate, polyethylene-vinyl alcohol, and polyvinylchloride. Preferably, the material is capable of being subjected to injection-mold procedures, relatively inexpensive, and somewhat compressible, particularly in the area of reservoir portion 10. Most preferably, the material is polyethylene.

Reservoir portion 10 is constituted by a chamber bounded by a pair of spaced, flat, generally parallel walls, 11 and 12. Preferably, walls 11 and 12 are of sufficient thickness that they are both compressible. By "compressible" is meant that when external pressure is applied thereto, walls 11 and 12 are capable of slightly moving in the direction of the applied pressure and are capable of resuming their approximate original position after release of pressure. For example, when compressed by the applied pressure of a finger and a thumb. Such pressure is preferably applied after a sample carrier (not shown) has been added to the vial. Beneficially, the application and release of such pressure (i.e., "agitation") aids in the release of the sample from the carrier into the extraction liquid. In this regard, the portion of walls 11 and 12 bounding the area between the walls (i.e., portions 11a and 12a of walls 11 and 12, respectively) are preferably substantially non-parallel with each other. By "substantially non-parallel" is meant that these portions of the walls further comprise features that are out of the general plane of a straight line defined by walls 11 and 12. For example, a series of ridges (not shown) can be located along walls 11a and 12a; alternatively, deformations (i.e., indentations, protrusions, etc.) can be incorporated along walls 11a and/or 12a. The function of such ridges is to assist in agitation of the extraction liquid and the sample carrier. I.e., as walls 11 and 12 are compressed, the increased surface area of walls 11a and 12a occasioned by such ridges increases the agitational movement of the liquid, thus increasing the likelihood of entry of additional sample material into the liquid.

Preferably, walls 11 and 12 further include "grip assisters" 15 (shown with respect to wall 11 in FIG. 1), e.g., a series of ridges which allow the user to more readily maintain a firm grip on device 100 for purposes of, e.g., compression of walls 11 and 12 for agitation of the liquid and/or release of the liquid onto an diagnostic test platform. As should be apparent, such grip assisters can be of any shape; the function thereof is to assist in the handling of device 100.

Figure 3:
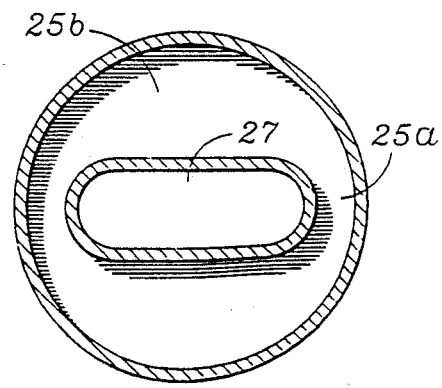
FIG. 3 is a cross-sectional view taken through line 3—3 of FIG. 1.

Neck portion 20 is integral with reservoir portion 10. Most preferably, neck portion 20 comprises a channel 25 for receiving a removable cap 200; channel 25 is defined by walls 11 and 12 and portions 21 and 22 of neck 20. Referencing FIG. 3, region 25a of channel 25 is smaller than region 25b of channel 25; beneficially, cap 200 can be configured so that it fits snugly within region 25a of channel 25, i.e., the width of portion 200a of cap 200 is configured to fit within region 25a of channel 25. When inserted within channel 25, cap 200 is most preferably rigidly maintained therein. By "rigidly maintained" is meant that a user must take affirmative steps to remove cap 200 from device 100, i.e., either by pulling cap 200 from channel 25 or by "screwing" cap 200 from channel 25. The intent is that once cap 200 is within channel 25, it will not be displaced therefrom due to, e.g., tipping of device 100, etc. Cap 200 preferably comprises handle 210 for purposes of gripping thereof.

Neck portion 20 further comprises opening 27 into reservoir portion 10. Opening 27 is configured to receive both the extraction liquid and a sample receiving platform. Advantageously, opening 27 can be covered with a removable, chemically inert material, for example a thin film of paraffin or plastic-backed foil (not shown). The intent of such material is to, e.g., prevent evaporation of the extraction liquid, and to add an extra measure of security vis-a-vis leakage of such liquid. Prior to insertion of a sample carrier through opening 27, such material can be removed and, e.g., discarded or re-applied to opening 27 after insertion of the sample carrier into reservoir portion 10.

At the opposite end of reservoir portion 10 relative to neck portion 20 is nozzle portion 30 which is most preferably angularly offset with respect to the longitudinal extent of walls 11 and 12. By "angularly offset" is meant that wall portions 31 and 32 are not in the same longitudinal plane as walls 11 and 12 of reservoir 10 such that, for example, the width X between the walls 11 and 12 is greater than the width Y between the walls 31 and 32. This configuration, therefore, has a somewhat "funnel" shape which descends to a leading end 35 of the nozzle portion 30. The leading end 35 is configured such that an extraction liquid comprising sample can be released therefrom. The distance between portion 35a and 35b of leading end 35 is preferably spaced such that the liquid droplets exiting therefrom are capable of being adequately controlled. By "adequately controlled" is meant that, preferably, liquid does not rapidly exit the reservoir portion without inward pressure on walls 11 and 12. Preferably, the distance between portions 35a and 35b is such that the surface tension of the liquid has a tendency to substantially remain within reservoir portion until released via applied pressure to walls 11 and 12. Preferably, the distance between portions 35a and 35b is between about 0.02 and about 0.15 inches, more preferably between about 0.03 and about 0.06 inches, and most preferably about 0.047 inches.

Most preferably, leading end 35 further comprises an annulus 40 projecting in an upwardly direction into nozzle portion 30. Annulus 40 assists in restricting and regulating the flow of liquid through leading end 35. The opposing sides 40a and 40b of annulus 40 can be either substantially parallel or substantially non-parallel depending on the necessity for controlling the liquid flow. I.e., by directing the upper most portions 40a and 40b of annulus 40 towards each other (i.e., sides 40a and 40b are substantially non-parallel) the distance between 40a and 40b gradually decreases, thus decreasing the area for release of liquid.

In configurations of the device where the release of solid-type materials through leading end 35 is a consideration, screening means (not shown) can be positioned across leading end 35 (or, in an equivalent manner, across nozzle portion 30 and/or reservoir portion 10) to prevent the release thereof. Screening means such as mesh are well known and will not be discussed herein in detail. Those in the art can readily select a screening means that is capable of being utilized in conjunction with biological and chemical materials, and which has sufficiently sized openings that allow for the release of liquid to the exclusion of particulate materials.

Figure 2:
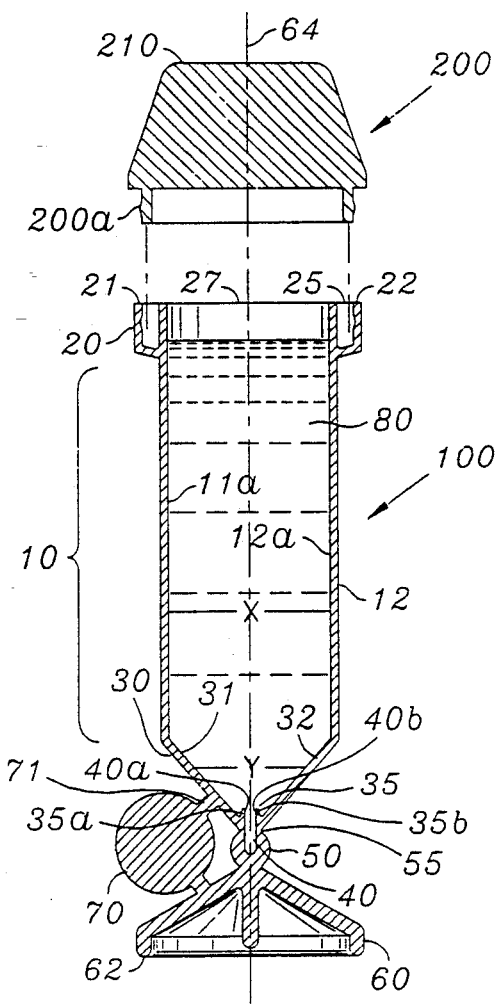
FIG. 2 is a cross-sectional view taken through line 2—2 of FIG. 1.

Positioned at the terminal end of leading end 35 is a sealing closure, generally depicted as 50 in FIGS. 1 and 2. Sealing closure 50 is connected to leading end 35 by line of weakness 55 (FIG. 2); when line of weakness 55 is broken, thus freeing sealing closure 50 from device 100, a discharge opening (not shown) is presented from which materials within reservoir portion 10 can be released. Line of weakness 55 is preferably configured such that it is easily broken, for example, by gentle movement of sealing closure 50 along line of weakness 55. However, in an equivalent manner, line of weakness 55 need not be broken by such movement, but can be cut using any conventional cutting tool. However, it is preferred that the former approach be utilized in order to avoid possible contamination and/or cross-contamination which could be occasioned by such a cutting tool.

Most preferably, sealing closure 50 is connected to base 60; a purpose for base 60 is that it is capable of allowing device 100 to be positioned in an upright orientation, i.e., the device including base 60 is "free-standing". Such a configuration is beneficial in that it can allow for introduction of a sample carrier to device 100 without the need to handle the device. The base 60 includes a rim or support surface 62 that is generally perpendicular to a central axis 64 of the vial 100, to make the vial 100 "free-standing" as just described. Beneficially, support mechanism 70 can be positioned between base 60 and nozzle 30 for an added degree of rigidity and support; as is appreciated, when support mechanism 70 is utilized, the connection 71 between mechanism 70 of nozzle 30 must also be a line of weakness as described above such that mechanism 70 is removed from device 100 when sealing closure 50 and base 60 are removed via line of weakness 55.

An extraction liquid (80) is most preferably included within reservoir portion 10 prior to insertion thereto of a sample carrier; however, in the case of, e.g., kits, extraction liquid can be included within another container and added to device 100 at an appropriate time. The extraction liquid is configured for use in the analysis of chemical or biochemical materials, such as those materials described above. Those skilled in the art are credited with readily selecting appropriate components for the extraction liquid in conjunction with the particular materials to be analyzed. For purposes of elucidation and not limitation, the following is directed to preferred extraction liquids utilized in conjunction with immunochromatographic assaying devices.

Generally, there are at least three criteria which must be considered when selecting an appropriate extraction liquid when used in conjunction with immunochromatographic assaying devices: (1) the extraction liquid must be compatible with a chemical or biochemical sample; (2) the extraction liquid must be compatible with the material used to manufacture vial 100; and (3) the extraction liquid must be compatible with the diagnostic testing matrix.

The first criteria is satisfied by utilizing a solution having a suitable pH, i.e., a pH within the range of between about 2.0 and about 12.0, preferably between about 6.0 and 8.0, and most preferably about 7.4. Exemplary solutions include, but are not limited to, phosphate buffered solutions, imidazole-hydrochloric acid ("HCl"), tris hydroxymethyl amino methane ("Tris"), Tris-HCl, 2-{[tris(hydroxymethyl)methyl]amino}ethane sulfoni acid (TES), N-2-hydroxyethylpiperazine-N'-2-ethane sulfonic acid (HEPES), triethanolamine hydrochloride and the salts thereof, piperazine-N,N'-bis (2-ethane-sulfonic acid) (PIPES), N-2-acetamide-2 aminoethanesulfonic acid (ACES), 3-(N-morpholino propanesulfonic acid (MOPS) and combinations of the foregoing. Preferably the buffer is a phosphate buffered solution having a pH of about 7.4, most preferably, the phosphate buffered solution is phosphate buffered saline.

The second criteria can most efficiently be satisfied by utilization of a chemically inert material for the construction of vial 100. Representative materials include, but are not limited to, polypropylene, polyvinylacetate polyethylene, polynitrile, polyethyleneterephthalate, polyethylene-vinyl acetate, polyethylene-vinyl alcohol, polyvinylchloride and combinations of the foregoing. Preferably, the material is polyethylene.

The third criteria is satisfied relative to the diagnostic testing matrix. With respect to immunochromatographic assaying devices, such matrices, by definition, have attached thereto immunological binding partners to analyte(s) in the sample. Thus, the extraction liquid must also be compatible therewith. As such, the same criteria (and buffers) set forth above for the first criteria are applicable to the third criteria. Additionally, it is typically necessary to include a non-specific binding inhibitor within the extraction liquid relative to the third criteria. Such a material functions to limit non-specific binding on the test matrix; exemplary materials include, but are not limited to, serum albumins such as, for example, human, bovine, goat, rabbit, sheep and horse serum albumins, ovalbumin, water soluble amino acid polymers, and combinations of the foregoing. Preferably, the non-specific binding inhibitor is bovine serum albumin, preferably within the range of about 0.5 to about 5.0% (weight/volume, "w/v"). When the diagnostic testing device is not an immunochromatographic device, such inhibitor is not required (although it can be utilized).

Accordingly, with respect to many immunochromatographic testing protocols, and in particular, protocols for the analysis of fecal occult testing via hemoglobin analysis, a particularly preferred extraction liquid comprises phosphate buffered saline having a pH of about 7.4 and about 1.0% (weight/volume) of bovine serum albumin.

Beneficially, the extraction liquid can, and preferably does, further comprise a preservative, such as, sodium azide, thimerosal or sodium benzoate. The extraction liquid can further, and preferably does, comprise at least one surfactant. The purpose of the surfactant is twofold: to assist in solubilization of the sample, and to assist in migration of the sample along the immunochemical test matrix. Exemplary surfactants include, but are not limited to, alkyl glucosides, betaines, bile acids, glucamides such as, for example, MEGA TM -8, -9 and -10 (available from Sigma Chemical Co.), and polyoxyethylenes, such as for example, the TRITON TM, GENAPOL TM (available from Hoechst Celanese), THESIT TM, BRIJ TM, TWEEN TM and PLURONIC TM surfactants (available from Sigma). Preferably, the surfactant is TRITON×100.

The size of vial 100 is such that it is preferred that between about 0.2 ml and 2 ml of extraction liquid is included therein (or, in the case of kits, added thereto). Most preferably, about 0.4 ml of an extraction liquid comprising phosphate buffered saline (pH 7.4), 1% bovine serum albumin (w/v), 3.6% Triton X-100 (volume/volume), and 0.1% (w/v) sodium azide is utilized.

The extraction vial can further incorporate additional features consistent with the objectives of the vial. For example, antibodies specific for interfering analytes (i.e., analytes in the sample that are preferably not added to the diagnostic matrix) can be covalently attached to the inner walls of the vial. The intent of such antibodies is to "remove" such interfering analytes from the liquid which is released into the matrix. Methodologies for covalently attaching antibodies to materials such as polyethylene are well known and will not be discussed herein in detail. Additionally, the extraction liquid itself can include (or can have added thereto), soluble antibodies to the desired analyte such that upon introduction of the test sample-comprising analyte, the soluble-antibody:analyte conjugate can be released onto the matrix. The extraction liquid can also comprise (or have added thereto), insolubilized antibody specific for interfering analytes; insolubilizing materials, such as latex particles, etc., are well known and will not be set forth herein detail. In such a configuration, it is preferred that a mesh material be utilized such that the insolubilized materials cannot pass through (or clog) the leading end of the nozzle.

Other materials can also be utilized in conjunction with objectives of the vial. For example, with fecal occult blood ("FOB") screening for colo-rectal cancer, it is known that blood from the lower gastrointestinal ("GI") tract may be indicative of such cancer, while blood from the upper GI tract (which may be indicative of an ulcer but which is not indicative of such cancer) can lead to so-called false-positive tests. I.e., for FOB screening, typically only lower GI blood is of import. It is also known that as blood passes through the stomach, hydrochloric acid converts the relatively uncharged hemoglobin in the blood to hematin and related hemoglobin breakdown products ("HBPs"); these are highly charged. Because blood from the lower GI tract has not passed through the hydrochloric acid in the stomach, the hemoglobin therein is not charged. These facets can be beneficially exploited.

For example, the extraction vial and/or liquid can include (or have added thereto) an ion exchange material such that hematin and HBPs which may be present in the sample are selectively attracted thereto via a charge interaction. Hemoglobin from lower GI bleeding, which is not charged, is not attracted to such material. Accordingly, use of such materials allows for the selective release of extraction liquid comprising (if present) lower GI tract hemoglobin onto the matrix. This protocol provides a highly specific screening protocol for colo-rectal cancer.

Ion exchange materials are well known and will not be discussed herein in detail. Materials which can serve as ion exchange media typically possess, but are not limited to, media with functional groups such as: alkylcarboxylates, alkylsulfonates, arylsulfonates, primary alkylamines, secondary alkylamines and quaternary amines. Specific ion exchange materials are available from Analytichem International, Inc. (Harbor City, Calif.); particularly preferred ion-exchange materials are, e.g., PSA, SAX and PRS. PSA is an anion exchanger, where the functional group is ethylenediamine-N-propyl; SAX is an anion exchanger, where the functional group is trimethylaminopropyl (chloride form); and PRS is a cation exchanger, where the functional group is sulfonylpropyl (sodium form).

While the foregoing has been described in considerable detail, it is to be understood that the foregoing description and drawings of preferred embodiments are not to be construed as limiting the disclosure or the claims to follow. Modifications which are within the purview of the skilled in the art are included with the scope of the disclosure and the claims to follow.

What is claimed is:

1. A vial suitable for use with an extraction liquid, comprising:
   a reservoir portion defining a chamber consisting of a pair of spaced, flat, generally parallel walls, the walls being compressible;
   a neck portion integral with the reservoir portion at a first end of the reservoir portion, the neck portion defining an opening into the reservoir portion and a channel surrounding the opening;
   a nozzle portion integral with the reservoir portion at a second end of the reservoir portion, the nozzle portion narrowing to a leading end and including a passage connecting with the chamber and the leading end;
   a sealing closure connected to the leading end by a line of weakness so as to close the leading end;
   a base integral with the sealing closure located opposite from the nozzle portion, the base including a support surface generally perpendicular to a central axis of the vial for stably supporting the vial in a generally vertical, upright position;
   a support tab integral with and extending between the nozzle portion and the base; and
   a cap including a portion adapted to be snugly received and removably rigidly maintained within the channel.

2. A vial as in claim 1 wherein the walls of the chamber include means for providing a gripping surface on the exterior of the walls.

3. A vial as in claim 1 wherein the vial further comprises an extraction liquid in the chamber of the reservoir portion adapted for use in the analysis of biological or chemical materials.

4. A vial as in claim 1, the nozzle portion further comprising an annulus projecting upward into the passage and located at the leading end of the nozzle portion.

* * * * *